United States Patent [19]

Gonzenbach

[11] Patent Number: 4,853,489

[45] Date of Patent: Aug. 1, 1989

[54] SELECTIVE CHLORINATION OF PARA-TERTIARY-BUTYTOLUENE

[76] Inventor: Hans U. Gonzenbach, 61 bis rue de Lyon, Geneva, Switzerland

[21] Appl. No.: 497,611

[22] Filed: May 28, 1983

[30] Foreign Application Priority Data

Jun. 3, 1982 [CH] Switzerland ............................ 3397/82
Apr. 19, 1983 [CH] Switzerland ............................ 2083/83

[51] Int. Cl.$^4$ .............................................. C07C 17/12
[52] U.S. Cl. ..................................................... 570/197
[58] Field of Search .................... 570/197; 204/163 R, 204/158 HA

[56] References Cited

U.S. PATENT DOCUMENTS

| 2,926,202 | 2/1960 | Lane | 570/197 |
| 3,442,960 | 5/1969 | DePuy et al. | 570/197 |
| 4,321,412 | 3/1982 | Schoch et al. | 570/197 |

FOREIGN PATENT DOCUMENTS

| 0045425 | 2/1982 | European Pat. Off. . |
| 81720 | 6/1982 | European Pat. Off. . |

OTHER PUBLICATIONS

Takeuchi et al., "Chemical Abstracts", vol. 89, p. 197188j.

Primary Examiner—Werren B. Lone

[57] ABSTRACT

A novel process for the selective chlorination of p-tert-butyltoluene to p-tert-butylbenzyl chloride.

7 Claims, No Drawings

SELECTIVE CHLORINATION OF PARA-TERTIARY-BUTYTOLUENE

THE INVENTION

The present invention is concerned with a novel process which can be used for the manufacture of p-tert-butylbenzene derivatives which are known to be useful chemical intermediates.

The process comprises reacting p-tert-butyltoluene with chlorine at temperatures of about −20° C. to +35° C., preferably about −10° C. to 10° C., under the influence of energy-rich radiation and/or in the presence of radical formers. If desired, the resulting p-tert-butylbenzyl chloride can be converted after purification, into p-tert-butylbenzaldehyde according to methods known per se.

It is a surprising and unexpected finding of this invention that the chlorination of p-tert-butyltoluene can be carried out with high selectivity (amount of benzyl derivative in the reaction product) even at high conversions (high ratio of converted, i.e. consumed, toluene derivative/starting material used). Radical chlorinations of p-tert-butyltoluene to the corresponding benzyl chloride have hitherto been considered uneconomical since there was always a considerable amount of chlorination of the tert-butyl group and, to a lesser extent, chlorination of the aromatic ring. This lack of selectivity was compounded by the fact that it would not be practical, if possible, to separate the p-tert-butylbenzyl chloride from the p-chloro-tert-butyltoluene and/or nuclear-chlorinated p-tert-butyltoluene on an industrial scale.

There accordingly exists a need for a practical and highly selective process for converting the p-tert-butyltoluene to the corresponding p-tert-butylbenzyl chloride which does not produce substantial amounts of these undesirable by-products. In accordance with this invention, the radical chlorination can now be carried out with a sufficiently high degree of selectivity by conducting the reaction at a relatively low temperature. Table I shows the remarkable improvement in selectivity when low temperatures are used.

TABLE I

Selectivity (expressed as the ratio of p-tert-butylbenzyl chloride formed to p-chloro-tert-butyltoluene formed) as function of the temperature.

| Conversion | Temperature [°C.] | Ratio |
|---|---|---|
| ⅔ | −15 | 36 |
|  | −14 | 26 |
|  | −5 | 20 |
|  | 0 | 14.5 |
|  | 23 | 5 |
|  | 26 | 4.4 |
|  | 100 | 2.2 |
| ≧80% | −14 | 42 |
|  | 6 | 38 |
|  | 9 | 33 |
|  | 27 | 17 |
|  | 47 | 5.9 |
|  | 100 | 2.4 |

DESCRIPTION OF THE PREFERRED EMBODIMENTS

In the present process the chlorine is suitably introduced into the p-tert-butyltoluene starting material in gaseous form. It can be convenient to conduct the reaction in the presence of an inert gas (e.g. nitrogen, argon etc.).

The chlorination can be carried out in the absence of a solvent or in the presence of a suitable solvent. Examples of such solvents are inert, especially halogenated, hydrocarbons such as carbon tetrachloride or chlorinated benzenes.

The reaction can be carried out at atmospheric pressure or under elevated pressure, especially slightly elevated pressure. The reaction can also be carried out via a batch process or via a continuous process.

The reaction is carried out at about −20° C. to +35° C., especially at about −10° C. to +10° C. It is, however, also possible to carry out the reaction at temperatures below −20° C., but this is economically less attractive. While somewhat less selective, suitable results can be obtained by running the reaction at about 5° C. to 35° C., especially at 15° C. to 25° C. At these higher temperatures the reaction proceeds more rapidly and less cooling is required.

The exothermic reaction is temperature controlled by means of a suitable cooling apparatus (e.g. a water-bath or cooling coils).

The energy required for the dissociation of the halogen molecules into atoms (radicals) is conveniently brought about by the influence of energy-rich radiation. Irradiation with UV-illuminators (e.g. by means of a mercury medium-pressure or high-pressure lamp) is preferred.

Other light sources can, however, also be used in the present process. It is a condition in each case that their radiation energy is sufficient in order to split the chlorine molecules into radicals, i.e. in the spectrum of the light source there must be present a sufficient amount with wavelengths of less than 488 nm. Examples of these other light sources are sunlight, fluorescence lamps, incandescent lamps, lasers etc.

So-called radical formers can also be used to split the chlorine molecule into radicals. Suitable radical formers for this purpose are those organic peroxides customarily used for side-chain chlorinations, azoisobutyronitrile etc., which can be activated (e.g. thermally or by light) in the temperature range used in accordance with the invention.

The chlorine introduction and radical formation are conveniently coordinated with one another so that all chlorine is absorbed (i.e. no chlorine escapes from the reaction mixture).

The molar ratio of chlorine to converted starting material is 1:1. It can, however, also be lower (e.g. 0.5:1 to 0.9:1), for example where the reaction is interrupted prematurely.

Such a premature interruption of the reaction can be advantageous, especially when the reaction is carried out in the upper temperature range, i.e. at 10°–35° C., in order to minimize the formation of high-boiling constituents, (e.g. dichlorinated products etc.). In such cases, any unreacted p-tert-butyltoluene can be conveniently recovered, e.g. by distillation.

The p-tert-butylbenzyl chloride obtained is conveniently purified by distillation, and can be obtained in a purity of at least 95%. The chloride can, however, also be used in the crude state.

The optional conversion of p-tert-butylbenzyl chloride into p-tert-butylbenzaldehyde can be carried out according to methods known per se; for example, by reaction with hexamethylenetetramine (Sommelet reaction, see Houben-Weyl, Methoden der organischen Chemie, Volume 7/1, page 194, G. Thieme, Stuttgart, 1954).

The p-tert-butylbenzyl chloride can also be hydrolyzed to p-tert-butylbenzyl alcohol or can be used as an alkylating agent etc.

The hydrochloric acid vapors which are formed in the reaction can be absorbed, for example, by means of a usual gas washing plant. When water is used as the washing liquid, aqueous hydrochloric acid is obtained which is a useful reagent and can be used as such.

ILLUSTRATION OF THE EMBODIMENTS

The following Example illustrates the present invention:

EXAMPLE

A. Chlorination of p-tert-butyltoluene (a) 50 g of p-tert-butyltoluene are placed in a round flask provided with a thermometer, magnetic stirrer, chlorine inlet tube, reflux condenser and a hydrogen chloride absorption apparatus which is filled with water. A mercury medium-pressure lamp (250 W) adjacent to the reaction vessel is switched on and thereupon the chlorine introduction is commenced while stirring. The reaction vessel is cooled by means of a cooling bath so that the temperature does not exceed 30° C. After 80% of the p-tert-butyltoluene have reacted (GC), the reaction is interrupted; nitrogen is blown through the vessel and the product is subsequently distilled. 9 g of p-tert-butyltoluene are recovered and 35 g of p-tert-butylbenzyl chloride with a purity of 95% (NMR/GC) are obtained. The distillation also yields 4 g of p-tert-butylbenzal chloride, 8 g of p-chloro-tert-butylbenzyl chloride and 5 g of residue.

(b)–(d) Further chlorinations were carried out in the same manner, the amount of p-tert-butyltoluene, the temperature and the conversion being varied. The results are compiled in Table II.

TABLE II

| Example | Temperature [°C.] | p-Tert-butyltoluene amount used [g] | p-Tert-butyltoluene recovered % | p-Tert-butylbenzyl chloride yield % | p-Tert-butylbenzyl chloride purity GC % |
|---|---|---|---|---|---|
| (a) | ≦30 | 50 | 18 | 56 | 95 |
| (b) | −14 | 100 | — | 83 | 97 |
| (c) | −15 | 150 | 11 | 75 | 97.5 |
| (d) | −7 | 500 | 7 | 84 | 95.5 |

The yields given relate to isolated (distillation) material without regard to the recovered p-tert-butyltoluene. (Yields based on converted starting material would naturally be higher). The purity was determined by gas chromatography and confirmed by NMR. The impurities consist mainly of about equal parts of p-chloro-tert-butyltoluene and m-tert-butylbenzyl chloride. The latter is formed from the m-tert-butyltoluene which is already present to about 3–6% in commercial qualitities of p-tert-butyltoluene.

(e) A series of experiments was carried out in the same manner and only the temperature was varied. After ⅔ of the p-tert-butyltoluene had been consumed, the ratio of p-tert-butylbenzyl chloride formed to p-chloro-tert-butyltoluene formed was determined by gas chromatography. The results are compiled in Table I presented earlier.

(f) A further series of experiments was analyzed after a conversion of 80% or more. The results are also given in Table I.

B. Conversion of p-tert-Butylbenzyl chloride to Aldehyde 17 g of hexamethylenetetramine, 9 ml of water, 6 ml of ethanol and 21.5 g of 95% p-tert-butylbenzyl chloride are added to a three-necked flask provided with a thermometer, magnetic stirrer and reflux condenser. The mixture is now warmed slowly to 45° C. while stirring. At this temperature the mixture is initially slurry-like and thereafter thinly liquid. An exothermic reaction occurs. The temperature is held at 45° C. with the aid of an ice-bath until the reaction fades away. Thereupon the mixture is stirred with renewed warming at 45° C. for 30 minutes. The reflux condenser is now replaced by a distillation bridge and 5 ml of ethanol are distilled off from the mixture under a slight vacuum (70 Torr). Thereupon, the distillation bridge is removed and a water separator is attached, thus enabling the separated water to flow back into the reaction vessel. The water separator is filled with about 60 ml of water and 10 ml of toluene and the mixture is treated with 60 ml of water. The mixture is heated to 140° C. At the beginning of the steam distillation the pH-value is adjusted to 4.5–5 by means of 60% sulphuric acid. The liquid in the water separator is renewed several times. The organic phases are separated from the distillates and the aqueous fractions are extracted with ether. The ether extracts and organic phases are in each case combined and washed with, in each case, about 20 ml of 15% sulphuric acid, water, 10% sodium carbonate solution and finally again with water and then concentrated. There are thus obtained a total of 14.7 g of crude product which are fractionated at 17 Torr over a 5 cm Widmer column and give 11.8 g (60%) of p-tert-butylbenzaldehyde with a purity of 92% (NMR/GC).

I claim:

1. A process for the manufacture of p-tert-butylbenzyl chloride from p-tert-butyltoluene which comprises reacting said p-tert-butyltoluene with chlorine radicals generated from molecular chlorine at temperatures between −20° C. and 35° C.

2. A process according to claim 1 wherein the chlorine radicals are formed by irradiating molecular chlorine, in situ, with a radiation source emitting sufficient radiation with wavelengths of less than 488 nm.

3. The process of claim 1 wherein the chlorine radicals are formed in the presence of an organic peroxide or azoisobutyronitrile.

4. The process of claim 1 wherein the molar ratio of chlorine to p-tert-butyltoluene is from 0.5:1 to 1:1.

5. A process according to claims 1, 2, 3 or 4 wherein the temperature is maintained between +5° C. and +35° C.

6. A process according to claims 1, 2, 3 or 4 wherein the temperature is maintained between −10° C. to +10° C.

7. A process according to claims 1, 2, 3 or 4 wherein the temperature is maintained between +15° C. to +25° C.

* * * * *

UNITED STATES PATENT AND TRADEMARK OFFICE
CERTIFICATE OF CORRECTION

PATENT NO. : 4,853,489
DATED : August 1, 1989
INVENTOR(S) : Hans U. Gonzenbach

It is certified that error appears in the above-identified patent and that said Letters Patent is hereby corrected as shown below:

On the Title page, section [54], and at column 1, lines 2 and 3, correct the title "Selective Chlorination of Para-Tertiary-Butytoluene" to read --Selective Chlorination of Para-Tertiary-Butyltoluene--.

Add to the Title page --[73] Assignee: Givaudan Corporation, Clifton, N.J.--; and --Attorney, Agent, or Firm - Robert F. Tavares: Linda A. Vag--.

Signed and Sealed this

Twenty-sixth Day of February, 1991

*Attest:*

HARRY F. MANBECK, JR.

*Attesting Officer*  *Commissioner of Patents and Trademarks*